(12) United States Patent
Johnson et al.

(10) Patent No.: US 12,418,710 B2
(45) Date of Patent: Sep. 16, 2025

(54) SMART TOOTHBRUSH UTILIZING FLUORESCENCE AND INTRAORAL CAMERA

(71) Applicant: SOTA Precision Optics, Inc., Orange, CA (US)

(72) Inventors: Dustin Johnson, Fullerton, CA (US); Albert Kim, Orange, CA (US); Bumsuk Kim, Orange, CA (US)

(73) Assignee: SOTA PRECISION OPTICS, INC., Orange, CA (US)

( * ) Notice: Subject to any disclaimer, the term of this patent is extended or adjusted under 35 U.S.C. 154(b) by 987 days.

(21) Appl. No.: 17/016,035

(22) Filed: Sep. 9, 2020

(65) Prior Publication Data

US 2021/0085168 A1   Mar. 25, 2021

Related U.S. Application Data

(60) Provisional application No. 62/902,595, filed on Sep. 19, 2019.

(51) Int. Cl.
*A61B 1/24* (2006.01)
*A46B 7/04* (2006.01)
(Continued)

(52) U.S. Cl.
CPC ............... *H04N 23/56* (2023.01); *A46B 7/04* (2013.01); *A46B 9/04* (2013.01); *A46B 15/0022* (2013.01); *A46B 15/0034* (2013.01); *A61B 1/00016* (2013.01); *A61B 1/00042* (2022.02); *A61B 1/00105* (2013.01); *A61B 1/042* (2013.01); *A61B 1/043* (2013.01); *A61B 1/0669* (2013.01); *A61B 1/07* (2013.01); *A61B 1/24* (2013.01); *H04N 23/54* (2023.01); *A46B 2200/1066* (2013.01); *H04B 1/02* (2013.01)

(58) Field of Classification Search
CPC . A61B 1/00016; A61B 1/00105; A61B 1/042; A61B 1/043; A61B 1/07; A46B 7/04; A46B 9/04; A46B 15/0022; A46B 2200/1066
See application file for complete search history.

(56) References Cited

U.S. PATENT DOCUMENTS

6,202,242 B1 *   3/2001   Salmon .............. A46B 15/0044
                                                    433/29
2005/0050659 A1 *   3/2005   Chan .................. A46B 15/0036
                                                    433/29
(Continued)

*Primary Examiner* — Baisakhi Roy
(74) *Attorney, Agent, or Firm* — INNOVATION CAPITAL LAW GROUP, LLP; Vic Lin (57) ABSTRACT

A smart toothbrush system, utilizing fluorescence and an intraoral camera, includes a toothbrush handle with embedded electronics, detachable brush and intraoral camera heads, and wireless connectivity capability for communication with external devices. The detachable brush head system is capable of directing particular wavelengths of light to the oral cavity, producing visible fluorescence when incident upon certain biomaterials that are indicative of the presence of various dental conditions. The intraoral camera head is capable of directing the same wavelengths of light to the oral cavity to produce the same fluorescing effect and can be used to closely inspect or record the presence of harmful biomaterials indicative of dental health.

16 Claims, 3 Drawing Sheets

(51) Int. Cl.

| | |
|---|---|
| *A46B 9/04* | (2006.01) |
| *A46B 15/00* | (2006.01) |
| *A61B 1/00* | (2006.01) |
| *A61B 1/04* | (2006.01) |
| *A61B 1/06* | (2006.01) |
| *A61B 1/07* | (2006.01) |
| *H04N 5/225* | (2006.01) |
| *H04N 23/54* | (2023.01) |
| *H04N 23/56* | (2023.01) |
| *H04B 1/02* | (2006.01) |

(56) References Cited

U.S. PATENT DOCUMENTS

| | | | | |
|---|---|---|---|---|
| 2006/0281042 | A1* | 12/2006 | Rizoiu | A46B 7/04 |
| | | | | 433/29 |
| 2007/0271714 | A1* | 11/2007 | Adam | A61C 19/066 |
| | | | | 30/32 |
| 2008/0209650 | A1* | 9/2008 | Brewer | A61C 17/221 |
| | | | | 433/119 |
| 2011/0151394 | A1* | 6/2011 | Rizoiu | A61K 8/25 |
| | | | | 433/29 |
| 2013/0203008 | A1* | 8/2013 | Kressman | A61B 5/0071 |
| | | | | 433/27 |
| 2016/0037903 | A1* | 2/2016 | Lal | G01B 11/00 |
| | | | | 15/167.1 |
| 2016/0286948 | A1* | 10/2016 | Amron | A46D 1/0207 |
| 2017/0095320 | A1* | 4/2017 | Addington | A61B 1/0684 |
| 2019/0328234 | A1* | 10/2019 | Seibel | A61B 1/24 |
| 2020/0196871 | A1* | 6/2020 | Ortiz | A61B 1/053 |
| 2020/0359777 | A1* | 11/2020 | Pesach | A61C 9/006 |
| 2022/0273408 | A1* | 9/2022 | Lawrence | A46B 5/0004 |

* cited by examiner

SMART TOOTHBRUSH UTILIZING FLUORESCENCE AND INTRAORAL CAMERA

CROSS-REFERENCE TO RELATED APPLICATIONS

This application claims the benefit of priority of U.S. provisional patent application No. 62/902,595, filed Sep. 19, 2019, the contents of which are herein incorporated by reference.

BACKGROUND OF THE INVENTION

1. Field of the Invention

Embodiments of the invention relate generally to oral personal hygiene, home dental care, medical devices, the internet of things, tele-dentistry, and artificial intelligence. One specific embodiment of the disclosure relates to the utilization of violet light fluorescence and an intraoral camera within a smart connected toothbrush system that utilizes an embedded neural network to aid in the at-home detection of plaque and anomalous dental conditions, and to facilitate remote communication of dental health with a dental practitioner.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Digital imaging technology is widely used in the medical and dental fields. Dental practitioners routinely utilize imaging devices ranging from intraoral x-ray sensors and panoramic x-ray machines, to intraoral cameras and fluorescence-based caries and plaque detection devices. When used in the dental office setting, these devices are used to diagnose the condition of oral health by assisting with the detection of dental lesions and other dental health problems. While these technologies are prevalent in dental offices, they are not readily available for public purchase, or they are not allowed to be sold as consumer devices due to regulatory restrictions.

Intraoral cameras are visible light imaging devices with an exterior housing designed to facilitate use within the oral cavity. They are used predominantly as patient communication devices, enabling dentists to show images of a patient's dentition to the patient during or after an examination. This helps increase case acceptance by motivating the patient to accept treatment for what is visibly wrong with their teeth.

Some intraoral cameras include fluorescence-based caries and plaque detection capabilities. Such devices work by incorporating light emitting diodes (LEDs), lasers, or other light sources that emit light in the ultraviolet or near-ultraviolet wavelength band, oftentimes at or around 407 nm. This wavelength is optimal because it causes excitation in Protoporphyrin IX (PPIX) molecules resulting in 590 nm, 620 nm, and 635 nm emission (all visible orange-light or red-light wavelengths) and can also cause mature dental plaque to fluoresce at 600-700 nm (also visible orange-light or red-light wavelengths).

PPIX is a byproduct of active carious lesions, perhaps caused by bacterial biosynthesis that occurs during the process of tooth decay. The dentist may use such a device to collect one of many different types of information that guide diagnosis and treatment of the patient. The dentist may also use the images acquired of the fluorescence when presenting the case to the patient for treatment. Some intraoral cameras with caries detection capability also include technology for quantifying the extent of the carious lesions in order to provide the practitioner with the capability to record the condition of the lesions empirically over time.

Conventional toothbrushes are used for routine cleaning of teeth, gums, and the tongue and are generally comprised of a plastic handle with clusters of polyamide or polyester bristles attached to one end. More advanced toothbrushes may include metal alloy handles, battery powered motors which oscillate, spin, or vibrate, timers that indicate to the user when they have brushed their teeth for a sufficient amount of time, and replaceable brush heads that allow the user to reuse the base of the toothbrush including the aforementioned motors and batteries. Toothbrushes are typically used in combination with fluoride-based toothpaste and water.

There are many problems with dental hygiene in the United States. The average American brushes their teeth for less than half the time recommended by dentists (Academy of General Dentistry, 2014). Three out of four millennials brush only once a day, and 42% of people do not change their toothbrush or replaceable toothbrush head every three months (Electric Teeth, 2018). Finally, more than 91% of U.S. adults aged 20-64 have dental caries in permanent teeth (U.S. Department of Health and Human Services, 2012).

The internet of things, especially smart devices, have driven enormous growth in industries ranging from the hard sciences to marketing to social media, but research, development, and adoption of such technologies in the consumer dental space has lagged significantly. Most consumers still use conventional toothbrushes and other traditional dental hygiene products and devices, despite the problems that continue to exist in home dental care and dental hygiene.

In view of the foregoing, there is a need for smart oral care devices that can aid in the at-home detection of plaque and anomalous dental conditions, and to facilitate remote communication of dental health with a dental practitioner.

SUMMARY OF THE INVENTION

Embodiments of the present invention provide a smart toothbrush system utilizing visible light fluorescence of Protoporphyrin IX and plaque, in combination with an intraoral camera, wireless connectivity, and an inertial measurement unit.

Embodiments of the present invention provide a toothbrush system comprising a toothbrush handle; a removable toothbrush brush head attachable to an attachment end of the toothbrush handle; transparent bristles disposed on a distal end of the brush head; and one or more light sources configured to deliver light outward through the transparent bristles.

Embodiments of the present invention further provide a toothbrush system comprising a toothbrush handle; a removable toothbrush brush head attachable to an attachment end of the toothbrush handle; transparent bristles disposed on a distal end of the brush head; a camera head removably attachable to the toothbrush handle, the camera head operable to acquire an image; electrical contacts disposed adjacent the attachment end of the toothbrush handle; camera head electrical contacts disposed in the camera head, the camera head electrical contacts electrically connecting with the electrical contacts of the toothbrush handle when the camera head is attached to the toothbrush handle; one or more light sources configured to deliver light outward through at least one of the transparent bristles and a distal end of the camera head, wherein the one or more light sources emits light having a wavelength that, when incident upon surfaces within an oral cavity, is capable of producing detectable visible wavelength fluorescence.

Embodiments of the present invention also provide a method of detecting plaque or anomalous dental conditions comprising disposing a toothbrush system at least partially into an oral cavity, the toothbrush system having a toothbrush handle, a removable toothbrush brush head attachable to an attachment end of the toothbrush handle, transparent bristles disposed on a distal end of the brush head, and one or more light sources configured to deliver light outward through the transparent bristles; and illuminating the one or more light sources to illuminate inside the oral cavity, wherein the one or more light sources emits light having a wavelength that, when incident upon surfaces within an oral cavity, is capable of producing detectable visible wavelength fluorescence.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a system and method for a smart toothbrush system utilizing fluorescence and an intraoral camera. The system includes a toothbrush handle with embedded electronics, detachable brush and intraoral camera heads, and wireless connectivity capability for communication with external devices. The detachable brush head system is capable of directing particular wavelengths of light to the oral cavity, producing visible fluorescence when incident upon certain biomaterials that are indicative of the presence of various dental conditions. The intraoral camera head is capable of directing the same wavelengths of light to the oral cavity to produce the same fluorescing effect and can be used to closely inspect or record the presence of harmful biomaterials indicative of dental health.

As used herein, the term "fluorescence" refers to electromagnetic radiation emitted resulting from incident radiation of higher energy.

As used herein, the term "plaque" refers to dental biofilm or material that grows on surfaces within the oral cavity.

As used herein, the term "internet of things" refers to the extension of the internet to include common objects, including connectivity and the ability to communicate and exchange data.

As used herein, the term "smart device" refers to an electronic device that may connect to other devices or to networks of varying connectivity standards and protocols which may include Wi-Fi, Bluetooth, cellular networks, and more.

As used herein, the term "inertial measurement unit" or "IMU" refers to an electronic package that may measure and communicate specific force, angular rate, and orientation, possibly using a combination of an accelerometer, a gyroscope, and a magnetometer.

As used herein, the term "microcontroller" or "MCU" refers to an integrated circuit or collection of integrated circuits that contains one or more computer processing units, electronic memory, and input/output capability.

As used herein, the term "CMOS sensor" refers to an electronic element that converts visible light into electrical stimulus commonly used in digital cameras and video devices As used herein, the term "image signal processor" or "ISP" refers to a digital signal processor used for image processing.

As used herein, the term "metadata" refers to data that describes other data.

As used herein, the term "Bluetooth"® refers to one standard for short range wireless connectivity found in mobile phones, computers, and other devices.

As used herein, the term "violet light" refers to light having wavelengths between 380 nm and 450 nm.

As used herein, the term "Wi-Fi"® refers to one method by which computers, smart phones, or other devices may communicate wirelessly, oftentimes to create computer networks or to facilitate access to the internet through a router.

Finally, the terms "or" and "and/or" as used herein are to be interpreted as inclusive or meaning any one or any combination. As an example, "A, B, or C" or "A, B, and/or C" mean "any of the following: A; B; C; A and B; A and C; A, B, and C." An exception to this definition will occur only when a combination of elements, functions, steps, or acts are in some way inherently mutually exclusive.

Figure 1:
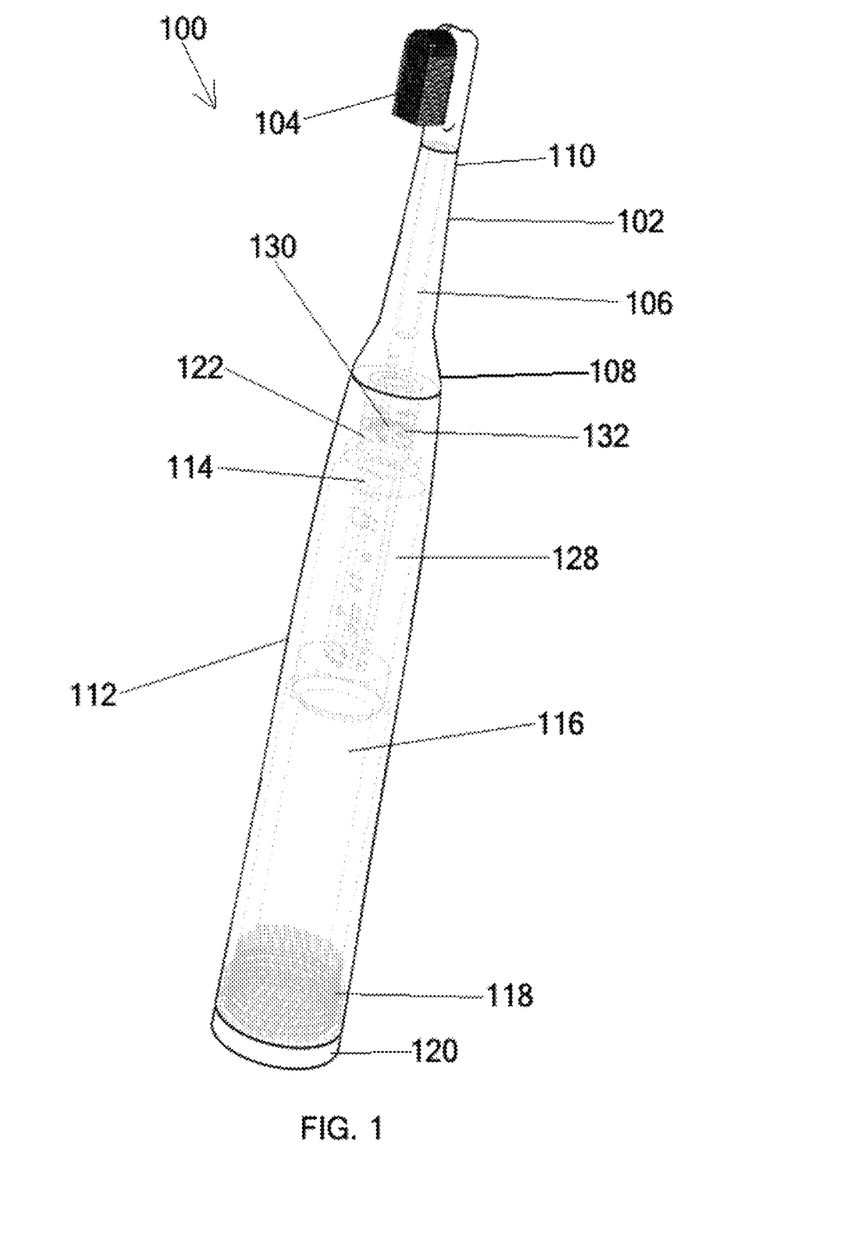
FIG. 1 illustrates a perspective view of a smart toothbrush with a removable brush head according to an exemplary embodiment of the present invention.
Figure 2:
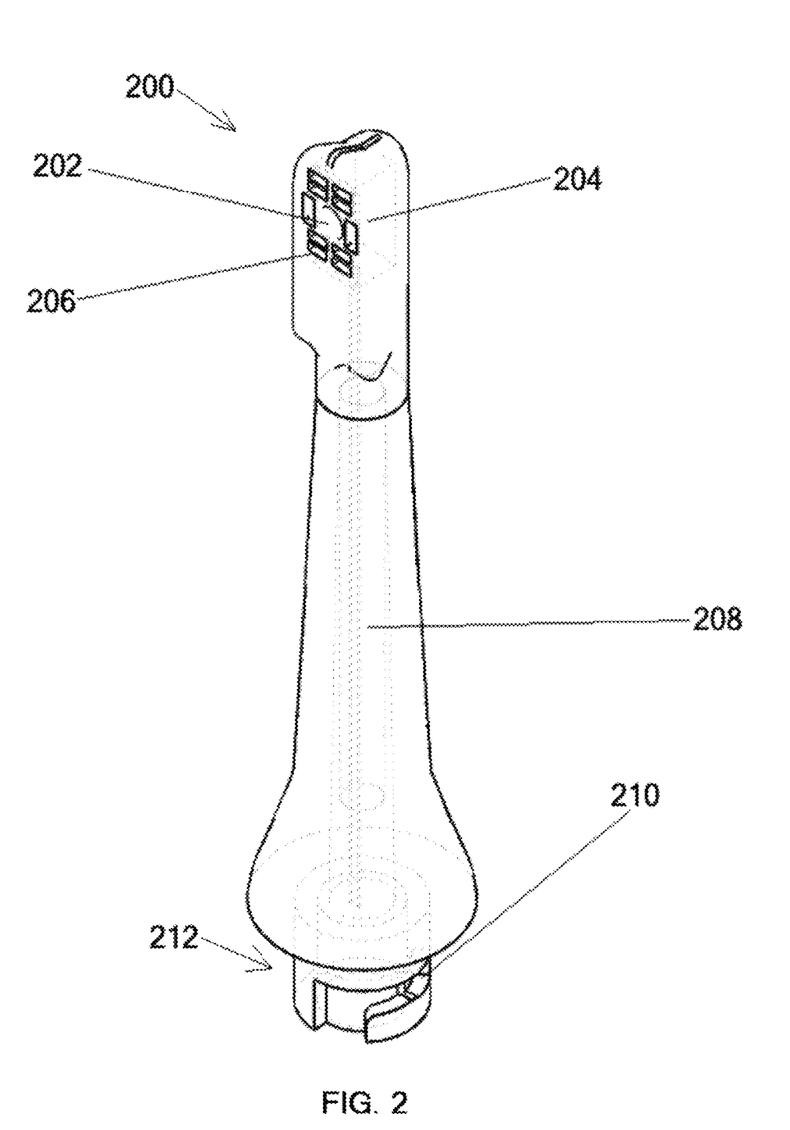
FIG. 2 illustrates a detailed view of an intraoral head for the smart toothbrush of FIG. 1.
Figure 3:
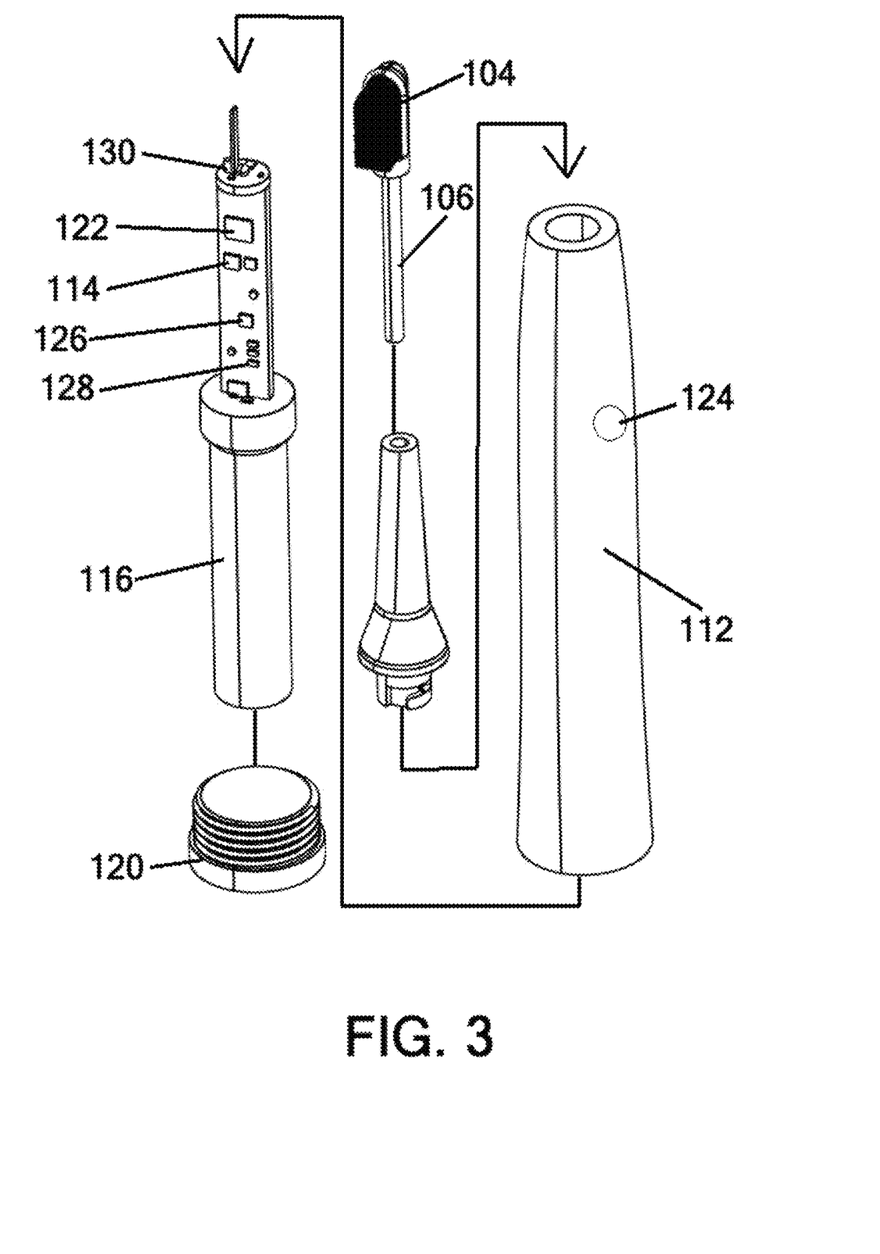
FIG. 3 illustrates an exploded perspective view of the smart toothbrush of FIG. 1.

Referring now to FIGS. 1-3, a smart toothbrush system 100 can include a detachable bristled toothbrush brush head 102 with transparent bristles 104. A light tube 106 can be disposed on an interior of the brush head 102, extending a proximal end 108 of the brush head 102 to a distal end 110 thereof. The light tube 106 can transmit light from a toothbrush handpiece 112 (also referred to as handle 112) to the bristles 104, as discussed below. In some embodiments, the light tube 106 may be transparent. The handle 112 can house various electronic components, electronically and operably connected to perform their required function. For example, the electronic components can include an inertial measurement unit 114, a battery 116, an inductive charging coil 118, an inductive charging base 120, a vibration motor 122, a multi-purpose button 124, a circuit board including a microcontroller 126 and antenna array 128 including wireless connectivity, such as Wi-Fi and/or Bluetooth capability and one or more violet LEDs 130.

As used herein, the term "transparent" refers to the ability to let light pass through a particular material. It should be understood that transparent elements may only need be transparent to the wavelengths of light of interest that need to pass through the transparent material.

In normal operation, the toothbrush 100 is stored on the inductive charging base 120, which is connected to a standard power outlet (not shown). The inductive charging base 120 can interact with the inductive charging coil 118 in the toothbrush handle 112, which provides power, charging the battery 116. Of course, other battery charging technologies may be used by the toothbrush 100 as may be understood by the art.

When a toothbrush brush head 102 is attached, the user may lift the handpiece 112 from the base, apply toothpaste to the bristles 104, and press the multi-purpose button 124 to start the vibration motor 112. The toothbrush head 102 may attach to the handpiece 112 using, for example, a cam mechanism, threaded screw-down mechanism, or spring-bar mechanism. The frequency of the vibration motor may be configured using the multi-purpose button. The user may toggle the violet LED(s) 130 on or off using the multi-purpose button in order to make apparent the presence of dental plaque or other fluorescent matter within the oral cavity. To illuminate the oral cavity with the violet light, the transparent tube 106 is used as a light pipe to transmit light from the top of the toothbrush handle 112, through the transparent tube 106, and into the transparent bristles 104, which direct the light into the mouth. The distal end 110 of the brush head 102 may also be selectively transparent to facilitate projection of light into the mouth. The transparent tube 106 may be plastic or any other transparent material such as glass and may be tapered at one end to facilitate aiming of the light.

The smart toothbrush system may communicate metadata about the brushing session to an application running on a device such as a smart phone or tablet computer using, for example, Bluetooth or Wi-Fi. Metadata may include, but is not limited to toothbrushing session duration, information about the position and motions of the toothbrush over that duration of time, battery charge level, vibration mode or level, and more. The toothbrush may be used on both human and animal subjects.

In one embodiment of the invention, the toothbrush handle 112 may include intraoral camera connector contacts 132 at one end. The contacts 132 may be used to permit the attachment of an intraoral camera head 200 comprised of an optical assembly 202, an image sensor 204, such as a CMOS sensor, LEDs 206, and a ribbon cable and/or wires 208 connected to contacts 210 at the proximal end 212 of the toothbrush camera head 200 to transfer the image data collected by the image sensor 204 to the intraoral camera contacts 132 of the handle 112. In some embodiments, the electrical contacts 132 are positioned opposite the toothbrush handle base, generally adjacent to the brush head attachment mechanism. In some embodiments, the electrical contacts 132 are oriented approximately normal to the surface of the toothbrush handle enclosure and generally normal to the lateral surface on the opposite side of the handle from the toothbrush handle base.

In such an embodiment, the camera head 200 may include white light LEDs, violet light LEDs, or a combination of the two types of LEDs, and the user may toggle between LED types or turn the LEDs on/off using a switch mechanism 214 located on the camera head 200 or via the multi-purpose button 124 or multiple buttons or capacitive switches on the handpiece 112.

The intraoral camera toothbrush head 200 may attach to the handle 112 using, for example but not limited to, a cam attachment, threaded attachment, or spring-bar mechanism. The intraoral camera connector contacts 132, 212 on both the handle 112 and intraoral camera head 200, respectively, may be liquid and dust proofed using any combination of O-rings, sealants, plastic molding, or other methods, to prevent liquid damage to the unit. The intraoral camera ISP may be configured in such a way as to reduce the impact of certain colors of violet light on the image, in order to enhance the visibility of red wavelengths corresponding to plaque or other fluorescent matter present within the oral cavity. With such an embodiment the user may use the intraoral camera brush head 200, along with their smart phone or other device, to view or save macro images of their teeth. When used in combination with the violet light LEDs, the user may take photos or video of the inside of their mouth that illustrate the presence or non-presence of plaque, carious lesions, or other fluorescent materials.

In one embodiment of the invention the intraoral camera headpiece may include bristles to facilitate brushing of the teeth while using the intraoral camera aspect of the smart toothbrush system.

In one embodiment of the invention, the intraoral camera components may be included in the handpiece in a manner that facilitates viewing of the toothbrush head and oral cavity so that a toothbrush headpiece may be used in tandem with the intraoral camera functionality. Such an embodiment may be achieved by positioning an optical light pipe within the toothbrush head.

In one embodiment of the invention the violet LEDs may be contained within the toothbrush head itself, powered by the connection of electrical contacts in the proximal end of the toothbrush head and the distal end of the toothbrush handle.

In one embodiment of the invention the brush head may use an oscillating slide mechanism or a rotating mechanism to assist with the brushing motion.

The below summarizes features according to various aspects of the present invention. Such features are non-limiting examples of various embodiments of the present invention.

1. A toothbrush handle comprising an enclosure containing a microcontroller, an inertial measurement unit, a battery, a charging circuit, electrical contacts, a button, a primary LED, a transparent window, a mechanism to attach a brush head or intraoral camera head, and an array of visible light LEDs;
2. The toothbrush handle of feature 1, wherein the electrical contacts are positioned opposite the toothbrush handle base, generally adjacent to the brush head attachment mechanism;
3. The method of feature 2, wherein the electrical contacts are oriented approximately normal to the surface of the toothbrush handle enclosure and generally normal to the lateral surface on the opposite side of the handle from the toothbrush handle base;
4. The toothbrush handle of feature 1 wherein the button is positioned adjacent to the exterior surface of the toothbrush handle along the longitudinal axis;
5. The method of feature 4 wherein the button is oriented approximately normal to the longitudinal axis of the toothbrush handle;
6. The toothbrush handle of feature 1 wherein the transparent window is positioned in front of the direction of emission of the primary LED generally normal to the lateral surface of the end of the toothbrush handle directly opposite the side of the toothbrush handle base;
7. The method of feature 6 wherein the transparent window is oriented approximately normal to the direction of emission of the primary LED, generally normal to the lateral surface on the opposite side of the handle from the toothbrush handle base;
8. The toothbrush handle of feature 7 wherein the primary LED emits a wavelength which when incident upon surfaces within the oral cavity may produce detectable visible wavelength fluorescence;
9. The toothbrush handle of feature 1 wherein the mechanism to attach the brush head positioned generally adjacent to the primary LED, opposite the base of the toothbrush head;
10. The toothbrush handle of feature 1 wherein the array of visible light LEDs is positioned adjacent to the exterior surface of the toothbrush handle along the longitudinal axis;
11. The method of feature 10 wherein the array of visible light LEDs is oriented in a direction that is generally normal to the surface of the toothbrush handle enclosure and the LED emission is generally directed away from the longitudinal surface;
12. A toothbrush brush head containing brush bristles and an attachment mechanism for connecting to a toothbrush handle;
13. The toothbrush brush head of feature 12 wherein a transparent tube is positioned along the longitudinal axis of the brush head and extends from the base of the toothbrush brush head, generally adjacent to the attachment mechanism, to the bristled end of the toothbrush brush head;
14. The method of feature 13 wherein the transparent tube terminates at the bristled end of the brush head in an approximately acute angle, directing light that is emitted through the brush head base and transparent tube into the adjacent toothbrush bristles;
15. The toothbrush head of feature 12 wherein the bristles of the brush head are generally optically transparent and whose optical properties facilitate the transmission of visible wavelengths of light from the proximal end to the distal end of each bristle;
16. The method of feature 15 wherein the bristles of the brush head are oriented in such a way that light entering the toothbrush bristles at the proximal end is directed through the toothbrush bristles at the distal end;
17. The toothbrush head of feature 12 wherein electrical contacts are positioned adjacent to the surface of the proximal end of the enclosure and contact the electrical contacts of feature 3 when attached to the toothbrush handle of feature 1 via the attachment mechanisms of features 1 and 12;
18. The toothbrush head of feature 12 wherein an LED is placed within the toothbrush head at or near the distal end;
19. The method of feature 18 wherein the LED emits a wavelength which when incident upon surfaces within the oral cavity may produce detectable visible wavelength fluorescence;
20. The toothbrush handle of feature 1 wherein an image signal processor is connected to a circuit board which is attached to the electrical contacts of feature 2;
21. A detachable toothbrush mounted intraoral camera head containing an image sensor, an optical assembly, an LED array, a ribbon cable or wires, electrical contacts, and a mechanism to facilitate attachment to the toothbrush handle of feature 1;
22. The intraoral camera head of feature 21 wherein the optical assembly is positioned adjacent to the image sensor at the distal end of the intraoral camera head enclosure;

23. The method of feature 22 wherein the optical assembly is oriented in such a manner as to direct light to the image sensor;
24. The intraoral camera head of feature 21 wherein the LED array components are positioned adjacent to the optical assembly;
25. The method of feature 24 wherein the LED array components are oriented approximately parallel to the plane of the objective lens of the optical assembly of feature 21;
26. The method of feature 21 wherein the LED array components include violet light LEDs which emit a wavelength that when incident upon surfaces within the oral cavity may produce detectable visible wavelength fluorescence;
27. The intraoral camera head of feature 21 wherein the electrical contacts are positioned at the proximal end of the intraoral camera head;
28. The method of feature 27 wherein the electrical contacts are positioned adjacent to the surface of the proximal end of the enclosure and contact the electrical contacts of feature 3 when attached to the toothbrush handle of feature 1 via the attachment mechanisms of feature 1 and 21;
29. The intraoral camera head of feature 21 wherein the electrical contacts of feature 27 and the electrical contacts of feature 3 are used to transfer information acquired by the image sensor of feature 21 to the image signal processor of feature 20;
30. The intraoral camera head of feature 21 wherein an image signal processor is positioned within the enclosure of the intraoral camera head and attached electronically to the image sensor, and additionally attached to the electronic contacts of feature 27;
31. The intraoral camera head of feature 21 and the toothbrush handle of feature 1 wherein the two components of the system are attached electronically via the electrical contacts of the respective features;
32. The method of connecting the intraoral camera head of feature 21 and the toothbrush handle of feature 1 wherein the two components of the system may interface such that an electronic image may be communicated to the microcontroller of feature 1 and subsequently communicated to other devices via the antenna array of feature 1;
33. A detachable intraoral camera head containing a light pipe and LEDs;
34. The detachable intraoral camera head of feature 33 wherein the light pipe is positioned longitudinally and spans the length from the proximal end to the distal end;
35. The method of feature 34 wherein the light pipe is approximately straight and of uniform thickness from one end of the head to the other;
36. The method of feature 34 wherein the light pipe is straight from the proximal end until near the distal end wherein an approximately 45 angle is cut prior to termination at the distal end and the pipe is extended in a manner normal to the longitudinal surface thereafter;
37. The detachable intraoral camera head of feature 33 wherein the LEDs are positioned near the distal end of the head adjacent to the terminating end of the light pipe;
38. The toothbrush head of feature 12 wherein the distal end of the brush head is partially transparent; and
39. The method of feature 38 wherein the transparent region of the brush head is oriented in such a manner as to maximize the transfer of light through the distal region adjacent to the bristles.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:
1. A toothbrush system comprising:
   a toothbrush handle;
   a vibration motor disposed within the toothbrush handle;
   a removable toothbrush brush head attachable to an attachment end of the toothbrush handle;
   transparent bristles attached to and extending directly from a distal end of the toothbrush brush head;
   one or more light sources disposed distal the vibration motor, within the toothbrush handle and directly below a proximal end of the brush head configured to deliver light to an interior of the toothbrush brush head, the light travelling outward through the transparent bristles; and a light tube extending from a proximal end to the distal end of the brush head, the light tube operable to deliver light from the one or more light sources to the transparent bristles, wherein:

the light travels along a light path directly from the light source to the light guide to the transparent bristles through the interior of the brush head; and the light has a wavelength that, when incident upon surfaces within an oral cavity, produces detectable visible wavelength fluorescence upon incidence to plaque or an anomalous dental condition, the light being violet light and the wavelength being from 380 nm to 450 nm.

2. The toothbrush system of claim 1, wherein the toothbrush handle includes a microcontroller, an inertial measurement unit, a battery, a charging circuit, electrical contacts, and a control button.

3. The toothbrush system of claim 1, further comprising electrical contacts disposed adjacent the attachment end of the toothbrush handle.

4. The toothbrush system of claim 3, further comprising a camera head removably attachable to the toothbrush handle, the camera head operable to acquire an image, the camera head attachable to the toothbrush handle in place of the removable toothbrush brush head at the attachment end.

5. The toothbrush system of claim 4, further comprising camera head electrical contacts disposed in the camera head, the camera head electrical contacts electrically connecting with the electrical contacts of the toothbrush handle when the camera head is attached to the toothbrush handle.

6. The toothbrush system of claim 4, further comprising one or more camera head light sources disposed to emit light away from the camera head.

7. The toothbrush system of claim 6, wherein the one or more camera head light sources include light emitting diode array components configured to emit light having a wavelength that, when incident upon surfaces within an oral cavity, produces detectable visible wavelength fluorescence.

8. The toothbrush system of claim 4, further comprising a camera head light tube extending from a proximal end to the distal end of the camera head, the light tube operable to deliver light from the one or more light sources to a distal end of the camera head.

9. The toothbrush system of claim 1, further comprising a wireless data transmitter operable to transmit data from the toothbrush system.

10. The toothbrush system of claim 9, wherein the data includes one or more of images, brushing activity and brushing time.

11. The toothbrush system of claim 1, wherein the distal end of the brush head is at least partially transparent, permitting light from the one or more light sources to be transmitted therethrough.

12. A toothbrush system comprising:
a toothbrush handle;
a vibration motor disposed within the toothbrush handle;
a removable toothbrush brush head attachable to an attachment end of the toothbrush handle;
transparent bristles attached to and extending from a distal end of the toothbrush brush head;
a camera head removably attachable to the attachment end of toothbrush handle in place of the removable toothbrush brush head, the camera head operable to acquire an image;
electrical contacts disposed adjacent the attachment end of the toothbrush handle;
camera head electrical contacts disposed in the camera head, the camera head electrical contacts electrically connecting with the electrical contacts of the toothbrush handle when the camera head is attached to the toothbrush handle;
one or more light sources disposed distal the vibration motor, within the toothbrush handle and directly below a proximal end of the brush head and configured to deliver light to an interior of the toothbrush brush head, the light travelling outward through at least one of the transparent bristles and a distal end of the camera head, wherein
the light has a wavelength that, when incident upon surfaces within an oral cavity, produces detectable visible wavelength fluorescence upon incidence to plaque or an anomalous dental condition, the light being violet light and the wavelength being from 380 nm to 450 nm.

13. The toothbrush system of claim 12, further comprising a light tube extending from a proximal end to the distal end of the brush head, the light tube operable to deliver light from the one or more light sources, disposed inside the handle, to the transparent bristles.

14. A method of detecting plaque or anomalous dental conditions, comprising:

disposing a toothbrush system at least partially into an oral cavity, the toothbrush system having a toothbrush handle, a vibration motor disposed within the toothbrush handle, a removable toothbrush brush head attachable to an attachment end of the toothbrush handle, transparent bristles attached to and extending directly from a distal end of the toothbrush brush head, one or more light sources disposed distal the vibration motor, within the toothbrush handle and directly below a proximal end of the brush head and configured to deliver light one or more light sources configured to deliver light to an interior of the toothbrush brush head, and a light tube extending from a proximal end to the distal end of the brush head, the light tube operable to deliver light from the one or more light sources to the transparent bristles, the light travelling outward through the transparent bristles; and illuminating the one or more light sources to illuminate inside the oral cavity, wherein:

the light travels along a light path directly from the light source to the light guide to the transparent bristles through the interior of the brush head; and the light has a wavelength that, when incident upon surfaces within an oral cavity, produces detectable visible wavelength fluorescence upon incidence to plaque or an anomalous dental condition, the light being violet light and the wavelength being from 380 nm to 450 nm.

15. The method of claim 14, further comprising:

removably attaching a camera head to the toothbrush handle; and acquiring an image with the camera head.

16. The method of claim 15, further comprising sending data from the toothbrush system to an external computing device, the data including the image.

* * * * *